United States Patent
Mo et al.

(10) Patent No.: US 11,980,337 B2
(45) Date of Patent: May 14, 2024

(54) HANDLE OF ENDOSCOPE WITH SELF-LOCKING ASSEMBLY AND INSERTION END POSITIONING ASSEMBLY

(71) Applicant: HUNAN VATHIN MEDICAL INSTRUMENT CO., LTD., Xiangtan (CN)

(72) Inventors: Wenjun Mo, Xiangtan (CN); Xiaofeng Jia, Xiangtan (CN); Guanhua Zhou, Xiangtan (CN); Peng Tang, Xiangtan (CN)

(73) Assignee: HUNAN VATHIN MEDICAL INSTRUMENT CO., LTD., Xiangtan (CN)

( * ) Notice: Subject to any disclaimer, the term of this patent is extended or adjusted under 35 U.S.C. 154(b) by 0 days.

(21) Appl. No.: 17/633,488

(22) PCT Filed: May 11, 2020

(86) PCT No.: PCT/CN2020/089654
§ 371 (c)(1),
(2) Date: Feb. 8, 2022

(87) PCT Pub. No.: WO2021/022858
PCT Pub. Date: Feb. 11, 2021

(65) Prior Publication Data
US 2022/0280024 A1    Sep. 8, 2022

(30) Foreign Application Priority Data

Aug. 7, 2019 (CN) .......................... 201910725815.9

(51) Int. Cl.
*A61B 1/00* (2006.01)
(52) U.S. Cl.
CPC ...... *A61B 1/00066* (2013.01); *A61B 1/00105* (2013.01)

(58) Field of Classification Search
CPC .. A61B 1/0066; A61B 1/00105; A61B 1/0052
(Continued)

(56) References Cited

U.S. PATENT DOCUMENTS 4,750,477 A * 6/1988 Wardle .................. A61B 1/307
600/149
4,765,312 A    8/1988 Sasa et al.
(Continued)

FOREIGN PATENT DOCUMENTS

CN    103654693 A    3/2014
CN    203988246 U    12/2014
(Continued)

*Primary Examiner* — John P Leubecker
*Assistant Examiner* — Li-Ting Song
(74) *Attorney, Agent, or Firm* — Bayramoglu Law Offices LLC

(57) ABSTRACT

A handheld end of an endoscope includes a housing, an insertion end positioning assembly and a self-locking assembly. The self-locking assembly is hinged to the housing. The housing includes an insertion port. The insertion end positioning assembly includes a positioning member, a first positioning nut and a threaded steel tube. The positioning member is inserted into the insertion port. The threaded steel tube is in threaded fit with the first positioning nut. The first positioning nut is fixed in the positioning member. The insertion end positioning assembly further includes a through hole and a fixing member. The fixing member is fit with the through hole to abut against the threaded steel tube. The threaded steel tube is fit with the positioning member to fix an axial position of the positioning member. A second nut is fit with a fixing screw to fix a rotational position of the positioning member.

10 Claims, 6 Drawing Sheets

(58) Field of Classification Search
USPC .......................................................... 600/131
See application file for complete search history.

(56) References Cited

U.S. PATENT DOCUMENTS

| | | | |
|---|---|---|---|
| 2004/0193011 A1 | 9/2004 | Akiba | |
| 2008/0287738 A1* | 11/2008 | Adachi | A61B 1/00042 600/118 |
| 2009/0010707 A1* | 1/2009 | Maruyama | F16B 35/005 403/201 |
| 2010/0312055 A1 | 12/2010 | Konstorum | |
| 2014/0135580 A1* | 5/2014 | Omoto | A61B 1/0016 600/146 |
| 2015/0126865 A1* | 5/2015 | Murai | A61B 8/4254 600/437 |
| 2017/0150870 A1 | 6/2017 | Koyama et al. | |
| 2017/0325659 A1 | 11/2017 | Wang et al. | |
| 2019/0167374 A1* | 6/2019 | Calavrezos | A61B 1/0014 |
| 2019/0350440 A1* | 11/2019 | Leong | A61B 1/0052 |
| 2020/0315426 A1* | 10/2020 | Yoshinaga | A61B 1/0055 |
| 2020/0323420 A1* | 10/2020 | Wu | A61B 1/00135 |
| 2020/0345218 A1* | 11/2020 | Lord | H04N 5/2624 |
| 2020/0359878 A1* | 11/2020 | Schwarz | A61B 17/32056 |
| 2021/0161555 A1* | 6/2021 | Winegar | A61B 1/0052 |
| 2022/0338725 A1* | 10/2022 | Murray | A61B 1/317 |
| 2022/0409019 A1* | 12/2022 | Mo | A61B 1/00066 |
| 2023/0020281 A1* | 1/2023 | Ono | A61B 1/00147 |

FOREIGN PATENT DOCUMENTS

| | | |
|---|---|---|
| CN | 107485360 A | 12/2017 |
| CN | 107613837 B | 8/2019 |
| CN | 110367907 A | 10/2019 |
| EP | 0306723 A1 | 3/1989 |
| JP | S62164432 A | 7/1987 |
| JP | H09276210 A | 10/1997 |
| JP | 2011177383 A | 9/2011 |
| JP | 2012065880 A | 4/2012 |
| JP | 2013202214 A | 10/2013 |
| JP | WO2015098210 A1 | 3/2017 |
| WO | 0022981 A1 | 4/2000 |

\* cited by examiner

US 11,980,337 B2

HANDLE OF ENDOSCOPE WITH SELF-LOCKING ASSEMBLY AND INSERTION END POSITIONING ASSEMBLY

CROSS REFERENCE TO THE RELATED APPLICATIONS

This application is the national phase entry of International Application No. PCT/CN2020/089654, filed on May 11, 2020, which is based upon and claims priority to Chinese Patent Application No. 201910725815.9, filed on Aug. 7, 2019, the entire contents of which are incorporated herein by reference.

TECHNICAL FIELD

The present invention relates to the technical field of endoscopes, and more particularly, to a handheld end of an endoscope.

BACKGROUND

At present, endoscopes are widely used in the medical field. The medical endoscope system is composed of an endoscope and an endoscope-specific processor. The endoscope includes an imaging unit such as a charge coupled device (CCD) image sensor for imaging an inside of a body cavity, and a first connector provided at an end of a universal cord. The endoscope-specific processor includes a second connector to which the first connector of the endoscope is detachably attached, a control unit for performing image processing on image data output by the endoscope, and a light source. In the endoscope system, the first connector of the endoscope is connected to the second connector of the endoscope-specific processor through an electrical contact, such that power is supplied from the endoscope-specific processor to the endoscope, and an image signal and a control signal are transmitted between the endoscope-specific processor and the endoscope.

However, there are the following problems when medical workers use the endoscope:
(1) How to adjust the connection between the handheld end of the endoscope and a plug-in end, and how to improve positioning.
(2) In experiments or operations, medical workers must always hold the handheld end of the endoscope while observing the internal structure of the human body, which makes their hands tired.

SUMMARY

The purpose of this section is to outline some aspects of the embodiments of the present invention and to briefly describe some preferred embodiments. Some simplification or omission may be made in this part as well as in the abstract of specification and the title of the disclosure of the present application to avoid blurring the purposes of this part, the abstract of specification and the title of the disclosure, and such simplification or omission cannot be used to limit the scope of the present invention.

The present invention is provided in view of the problems as mentioned above and/or existing in the prior art.

An objective of the present invention is to provide a handheld end of an endoscope.

To solve the above technical problems, the present invention adopts the following technical solution. A handheld end of an endoscope includes a housing, an insertion end positioning assembly and a self-locking assembly, where the self-locking assembly is hinged to the housing; the housing includes an insertion port; the insertion end positioning assembly includes a positioning member, a first positioning nut and a threaded steel tube; the positioning member is inserted into the insertion port; the threaded steel tube is in threaded fit with the first positioning nut; the first positioning nut is fixed in the positioning member; the insertion end positioning assembly further includes a through hole and a fixing member; and the fixing member is fit with the through hole to abut against the threaded steel tube.

In a preferred solution of the handheld end of an endoscope of the present invention, the positioning member may be provided with a limiting slot; the insertion end positioning assembly may further include a stop piece; the stop piece may be provided in the limiting slot, and a diameter of the stop piece may be greater than a diameter of the insertion port.

In a preferred solution of the handheld end of an endoscope of the present invention, the fixing member may include a second nut and a fixing screw; the second nut may be fixed to the through hole; and the fixing screw may be in threaded fit with the second nut.

In a preferred solution of the handheld end of an endoscope of the present invention, the insertion end positioning assembly may further include a locking member; an inner bottom of the locking member is provided with a straight clamping slot, and an inner wall of the locking member may be provided with an internal thread; a tail end of the positioning member may be provided with a straight fixing block; the straight fixing block may be fit with the straight clamping slot; the housing may further include a protective shell; the protective shell may be provided outside the insertion port, and may be fixedly connected to the insertion port; and the protective shell may be provided with an external thread, and the external thread may be fit with the internal thread.

In a preferred solution of the handheld end of an endoscope of the present invention, the self-locking assembly may include a toggle support, an elastic support and a toggle handle; the toggle handle may be sleeved on the toggle support, and may be movable along a sleeving direction; a shaft of the toggle support may pass through the housing, and may be connected to the elastic support on the other side; an inner side of the toggle support may be provided with a toggle lever and a friction piece; one end of the toggle lever may be hinged to the toggle handle, and the other end thereof may be not connected to the friction piece; the toggle lever may have an L-shaped cross section, with a middle bend fixed to the toggle support; and the toggle lever may be hinged to the toggle support through a pin.

In a preferred solution of the handheld end of an endoscope of the present invention, the self-locking assembly may further include a limiting member; the limiting member may include a fixing disc and a fitted disc; the fixing disc and the fitted disc may be fit with each other; the fixing disc may be fixed to a long shaft; and a limiting block may be provided on the fitted disc.

In a preferred solution of the handheld end of an endoscope of the present invention, reinforcing ribs may be further provided inside the housing; there may be two reinforcing ribs; and a movement space formed between the two reinforcing ribs may be fit with the limiting block.

In a preferred solution of the handheld end of an endoscope of the present invention, one end of the toggle lever may be provided with a fitting bump, and one end of the friction piece may be provided with a fitted bump; and a plane on which the fitting bump may be located may be opposite to a plane on which the fitted bump may be located, so that the fitting bump and the fitted bump are fit with each other.

In a preferred solution of the handheld end of an endoscope of the present invention, the toggle lever and the toggle handle may be hinged through a pin; a connecting end of the toggle lever may be provided with a long oval hole; and the pin may pass through the long oval hole to be fit with the toggle support.

In a preferred solution of the handheld end of an endoscope of the present invention, one end of the friction piece may be fixed to the other end of the elastic support through the long shaft.

The present invention has the following beneficial effects:
(1) The threaded steel tube is fit with the positioning member to fix an axial position of the positioning member. The second nut is fit with the fixing screw to fix a rotational position of the positioning member. The straight clamping slot is fit with the straight fixing block to fix a position of the insertion end.
(2) The toggle handle is moved to drive the toggle lever to move along with the toggle handle, and the tail end of the toggle lever is in contact with the friction piece. The friction piece moves back and forth, such that the elastic support is close to and away from the housing, and such that the self-locking of the toggle handle is realized through the contact between the friction piece and the tail end of the toggle lever. The self-locking of the endoscope is achieved by making the elastic support close to and away from the housing. The present invention features simple structure, low production cost and high work efficiency.

BRIEF DESCRIPTION OF THE DRAWINGS

To describe the technical solutions in the embodiments of the present invention more clearly, the following briefly describes the drawings required for describing the embodiments or the prior art. The drawings in the following description show merely some of the embodiments of the present invention, and those of ordinary skill in the art may still derive other drawings from these drawings without creative efforts.

DETAILED DESCRIPTION OF THE EMBODIMENTS

To make the above objectives, features and advantages of the present invention clearer, the specific implementations of the present invention are described in detail below with reference to the drawings of the specification.

Many specific details are set forth in the following description to facilitate full understanding of the present invention, but the present invention may also be implemented in other ways different from those described herein, similar derivatives may be made by those skilled in the art without departing from the connotation of the present invention, and therefore, the present invention is not limited by the specific embodiments disclosed below.

In addition, the "one embodiment" or "embodiments" herein refers to a particular feature, structure or characteristic that may be included in at least one implementation of the present invention. The phrase "in an embodiment" used multiple times herein refers to neither one same embodiment nor an individual or alternative embodiment mutually exclusive with other embodiment.

Embodiment 1

Figure 1:
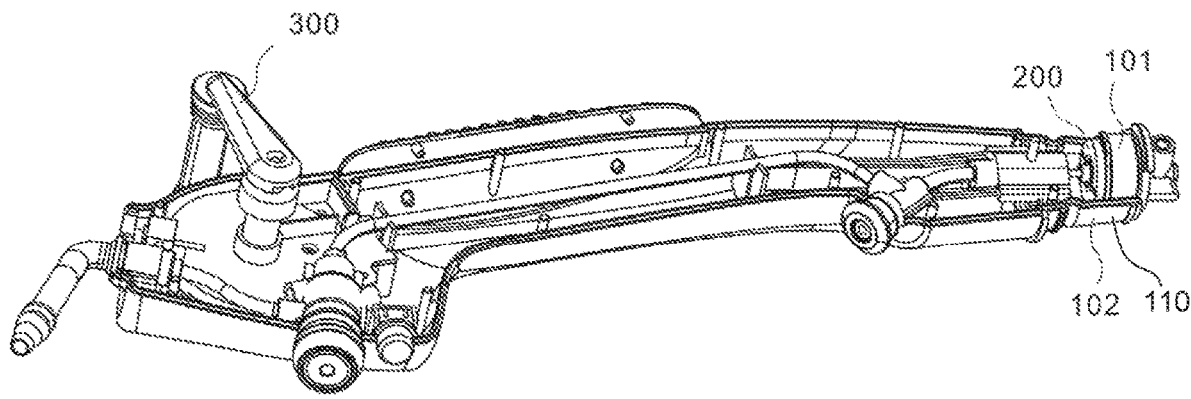
FIG. 1 is a partial structural view of a handheld end of an endoscope according to an embodiment of the present invention.
Figure 2:
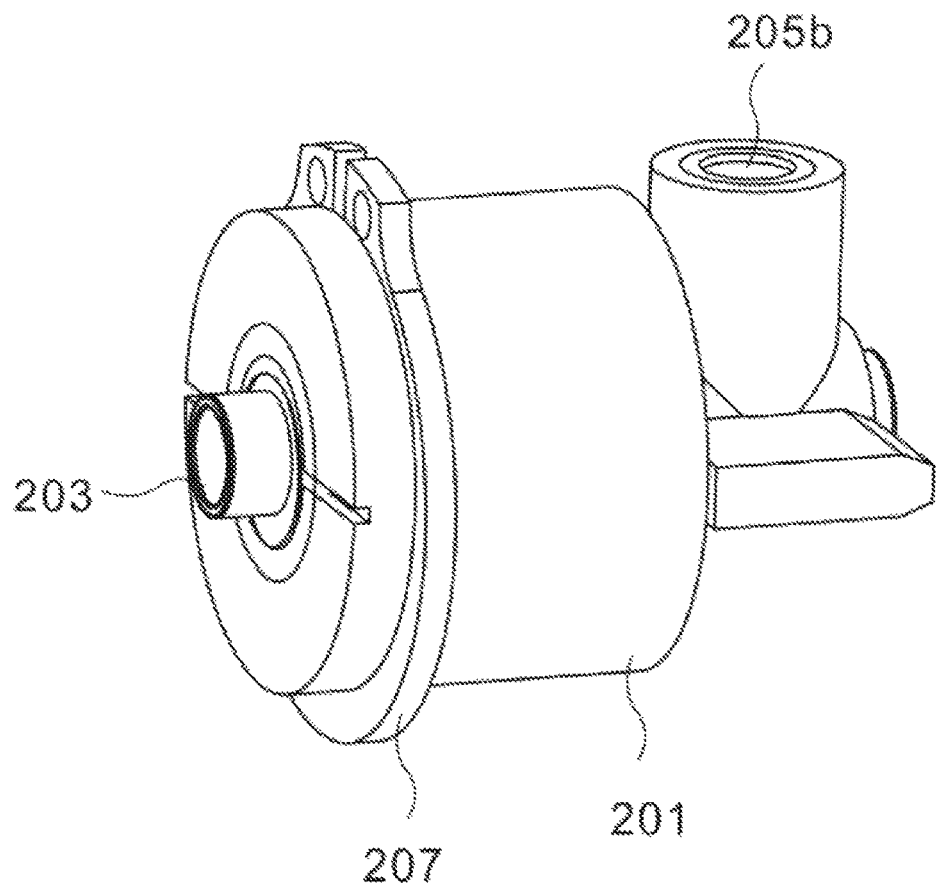
FIG. 2 is a full structural view of an insertion end positioning assembly of the handheld end of an endoscope according to an embodiment of the present invention.
Figure 3:
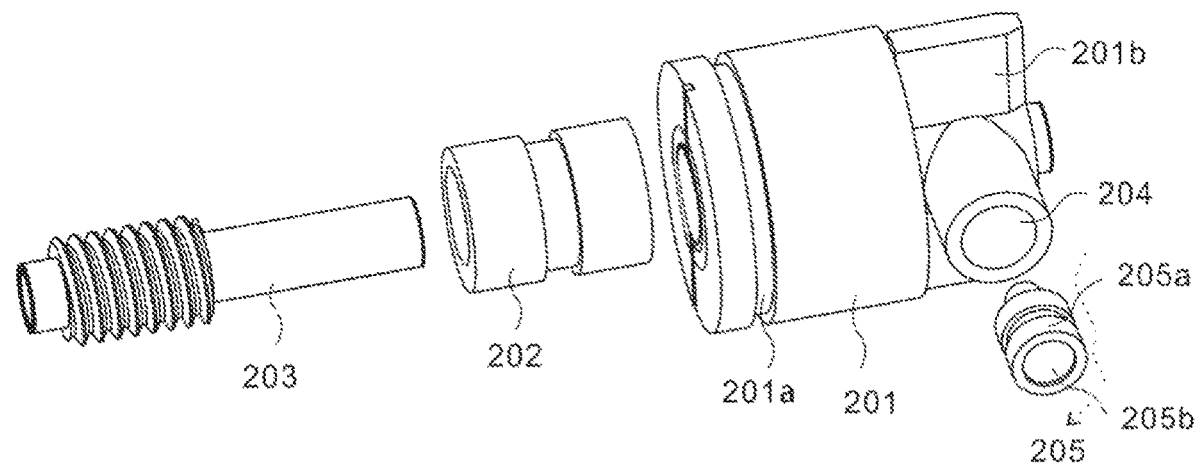
FIG. 3 is an exploded view of the insertion end positioning assembly of the handheld end of an endoscope according to an embodiment of the present invention.
Figure 4:
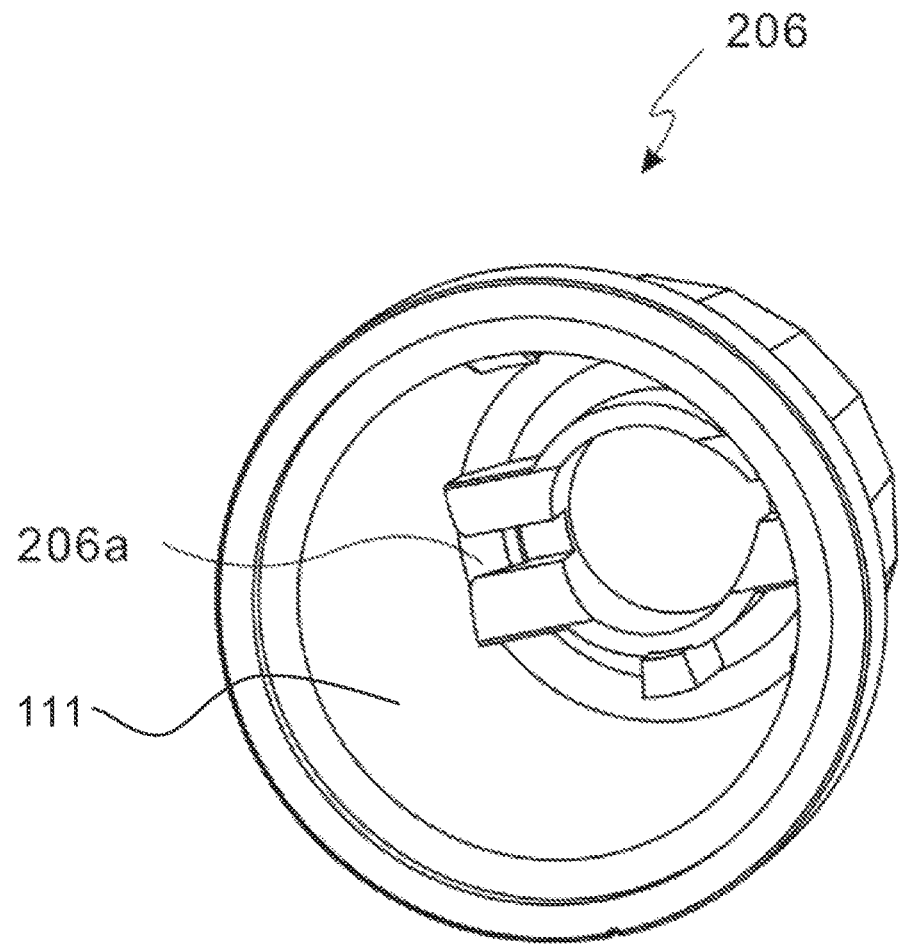
FIG. 4 is a full structural view of a locking member of the handheld end of an endoscope according to an embodiment of the present invention.
Figure 10:
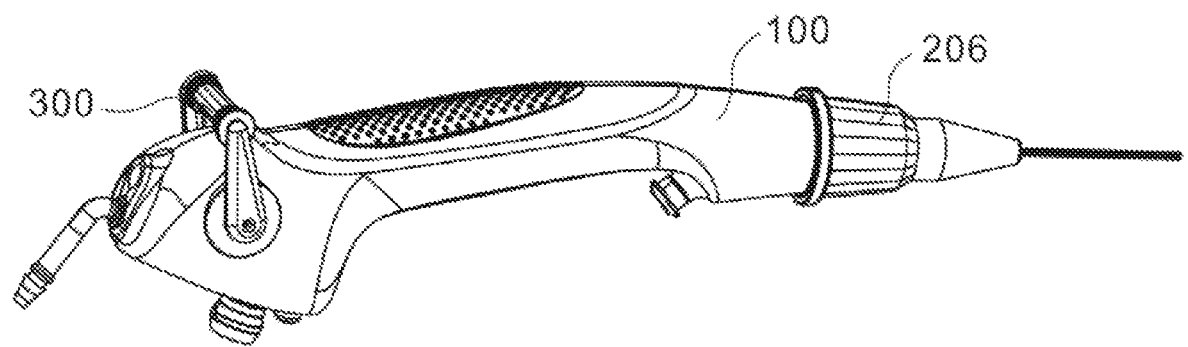
FIG. 10 is a full structural view of the handheld end of an endoscope according to an embodiment of the present invention.

Referring to FIGS. 1-4 and 10, the present invention provides a handheld end of an endoscope. The handheld end of the endoscope includes a housing 100, an insertion end positioning assembly 200 and a self-locking assembly 300. The insertion end positioning assembly 200 is fit with the housing 100 to fix an insertion end. The self-locking assembly 300 is hinged to the housing 100.

The housing 100 includes an insertion port 101. When the housing 100 and the insertion end positioning assembly 200 are fit, the insertion end positioning assembly 200 is inserted into the insertion port 101.

The insertion end positioning assembly 200 includes a positioning member 201, a first positioning nut 202, a threaded steel tube 203, a through hole 204 and a fixing member 205. The positioning member 201 is inserted into the insertion port 101. The threaded steel tube 203 is in threaded fit with the first positioning nut 202. The first positioning nut 202 is fixed in the positioning member 201. The fixing member 205 is fit with the through hole 204 to abut against the threaded steel tube 203.

The positioning member 201 is provided with a limiting slot 201a. The insertion end positioning assembly 200 further includes a stop piece 207. The stop piece 207 is provided in the limiting slot 201a, and a diameter of the stop piece 207 is greater than a diameter of the insertion port 101. In this way, when the positioning member 201 is inserted into the insertion port 101, the stop piece 207 clamps the positioning member 201 at the insertion port 101. When the positioning member 201 is pulled, the positioning member 201 will not disengage from the insertion port 101.

During assembly, the parts are fit with each other. When the positioning member 201 is snapped to the insertion port 101, the stop piece 207 only limits the axial movement of the positioning member 201. That is, the positioning member 201 may also be rotatable. In order to solve this problem, in this embodiment, the fixing member 205 is fit with the through hole 204 to abut against the threaded steel tube 203, thereby limiting the rotation of the positioning member 201.

It should be noted that the threaded steel tube 203 is provided with a cord connected to the endoscope. One end of the cord is fixed inside the housing 100, and the other end thereof passes through the threaded steel tube 203 and the insertion port 101. In order to fix the cord, in this embodiment, the fixing member 205 includes a second nut 205a and a fixing screw 205b. The second nut 205a is fixed to the through hole 204, and the fixing screw 205b is in threaded fit with the second nut 205a. The second nut 205a is fixedly connected to the through hole 204 by bonding or welding. When the fixing screw 205b is rotated, the fixing screw 205b is moved relative to the second nut 205a such that an end portion of an entry end of the fixing screw 205b presses the cord.

The working principle of this embodiment is as follows. In this embodiment, when the positioning member 201 is inserted into the insertion port 101, the stop piece 207 clamps the positioning member 201 at the insertion port 101. When the positioning member 201 is pulled, the positioning member 201 will not disengage from the insertion port 101. The second nut 205a is fixedly connected to the through hole 204 by bonding or welding. When the fixing screw 205b is rotated, the fixing screw 205b is moved relative to the second nut 205a such that an end portion of an entry end of the fixing screw 205b presses the cord.

Embodiment 2

Referring to FIGS. 1-4 and 10, a second embodiment of the present invention provides a handheld end of an endoscope. Different from the first embodiment, in the second embodiment, the insertion end positioning assembly 200 further includes a locking member 206. An inner bottom of the locking member 206 is provided with a straight clamping slot 206a, and an inner wall of the locking member 206 is provided with an internal thread reference number 111.

It should be noted that, in this embodiment, a tail end of the positioning member 201 is provided with a straight fixing block 201b. The straight fixing block 201b is fit with the straight clamping slot 206a.

Specifically, the handheld end of the endoscope includes a housing 100, an insertion end positioning assembly 200 and a self-locking assembly 300. The insertion end positioning assembly 200 is fit with the housing 100 to fix an insertion end. The self-locking assembly 300 is hinged to the housing 100.

The housing 100 includes an insertion port 101. When the housing 100 and the insertion end positioning assembly 200 are fit, the insertion end positioning assembly 200 is inserted into the insertion port 101.

The insertion end positioning assembly 200 includes a positioning member 201, a first positioning nut 202, a threaded steel tube 203, a through hole 204, a fixing member 205 and a locking member 206. The positioning member 201 is inserted into the insertion port 101, and a straight fixing block 201b is provided at a tail end of the positioning member 201. The threaded steel tube 203 is in threaded fit with the first positioning nut 202. The first positioning nut 202 is fixed in the positioning member 201. The fixing member 205 is fit with the through hole 204 to abut against the threaded steel tube 203. An inner bottom of the locking member 206 is provided with a straight clamping slot 206a, and an inner wall of the locking member 206 is provided with an internal thread reference number 111. The straight fixing block 201b is fit with the straight clamping slot 206a.

The positioning member 201 is provided with a limiting slot 201a. The insertion end positioning assembly 200 further includes a stop piece 207. The stop piece 207 is provided in the limiting slot 201a, and a diameter of the stop piece 207 is greater than a diameter of the insertion port 101. In this way, when the positioning member 201 is inserted into the insertion port 101, the stop piece 207 clamps the positioning member 201 at the insertion port 101. When the positioning member 201 is pulled, the positioning member 201 will not disengage from the insertion port 101.

During assembly, the parts are fit with each other. When the positioning member 201 is snapped to the insertion port 101, the stop piece 207 only limits the axial movement of the positioning member 201. That is, the positioning member 201 may also be rotatable. In order to solve this problem, in this embodiment, the fixing member 205 is fit with the through hole 204 to abut against the threaded steel tube 203, thereby limiting the rotation of the positioning member 201.

It should be noted that the threaded steel tube 203 is provided with a cord connected to the endoscope. One end of the cord is fixed inside the housing 100, and the other end thereof passes through the threaded steel tube 203 and the insertion port 101. In order to fix the cord, in this embodiment, the fixing member 205 includes a second nut 205a and a fixing screw 205b. The second nut 205a is fixed to the through hole 204, and the fixing screw 205b is in threaded fit with the second nut 205a. The second nut 205a is fixedly connected to the through hole 204 by bonding or welding. When the fixing screw 205b is rotated, the fixing screw 205b is moved relative to the second nut 205a such that an end portion of an entry end of the fixing screw 205b presses the cord.

Preferably, the housing 100 further includes a protective shell 102. The protective shell 102 is provided outside the insertion port 101, and is fixedly connected to the insertion port 101. The protective shell 102 is provided with an external thread reference number 110, and the external thread reference number 110 is fit with the internal thread reference number 111. The external thread reference number 110 of the protective shell 102 is fit with the internal thread reference number 111 of the locking member 206 to lock the position of a plug-in end.

The working principle of this embodiment is as follows. In this embodiment, when the positioning member 201 is inserted into the insertion port 101, the stop piece 207 clamps the positioning member 201 at the insertion port 101. When the positioning member 201 is pulled, the positioning member 201 will not disengage from the insertion port 101. The second nut 205a is fixedly connected to the through hole 204 by bonding or welding. When the fixing screw 205b is rotated, the fixing screw 205b is moved relative to the second nut 205a such that an end portion of an entry end of the fixing screw 205b presses the cord. The straight fixing block 201b is fit with the straight clamping slot 206a, and the external thread reference number 110 of the protective shell 102 is fit with the internal thread reference number 111 of the locking member 206, so as to position the locking member 206 and lock the position of the plug-in end.

Embodiment 3

Figure 5:
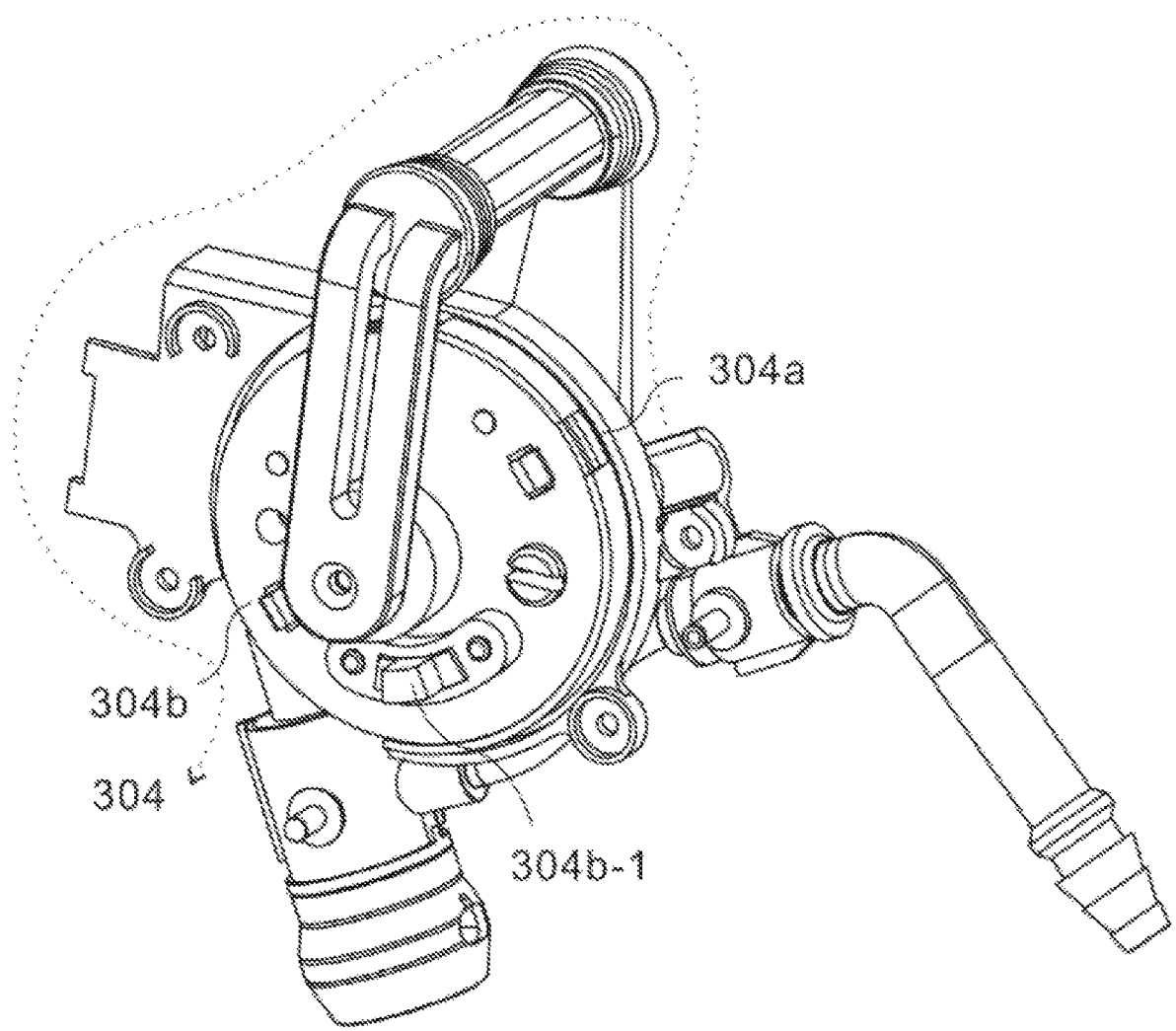
FIG. 5 is a partial structural view of a self-locking assembly of the handheld end of an endoscope according to an embodiment of the present invention.
Figure 6:
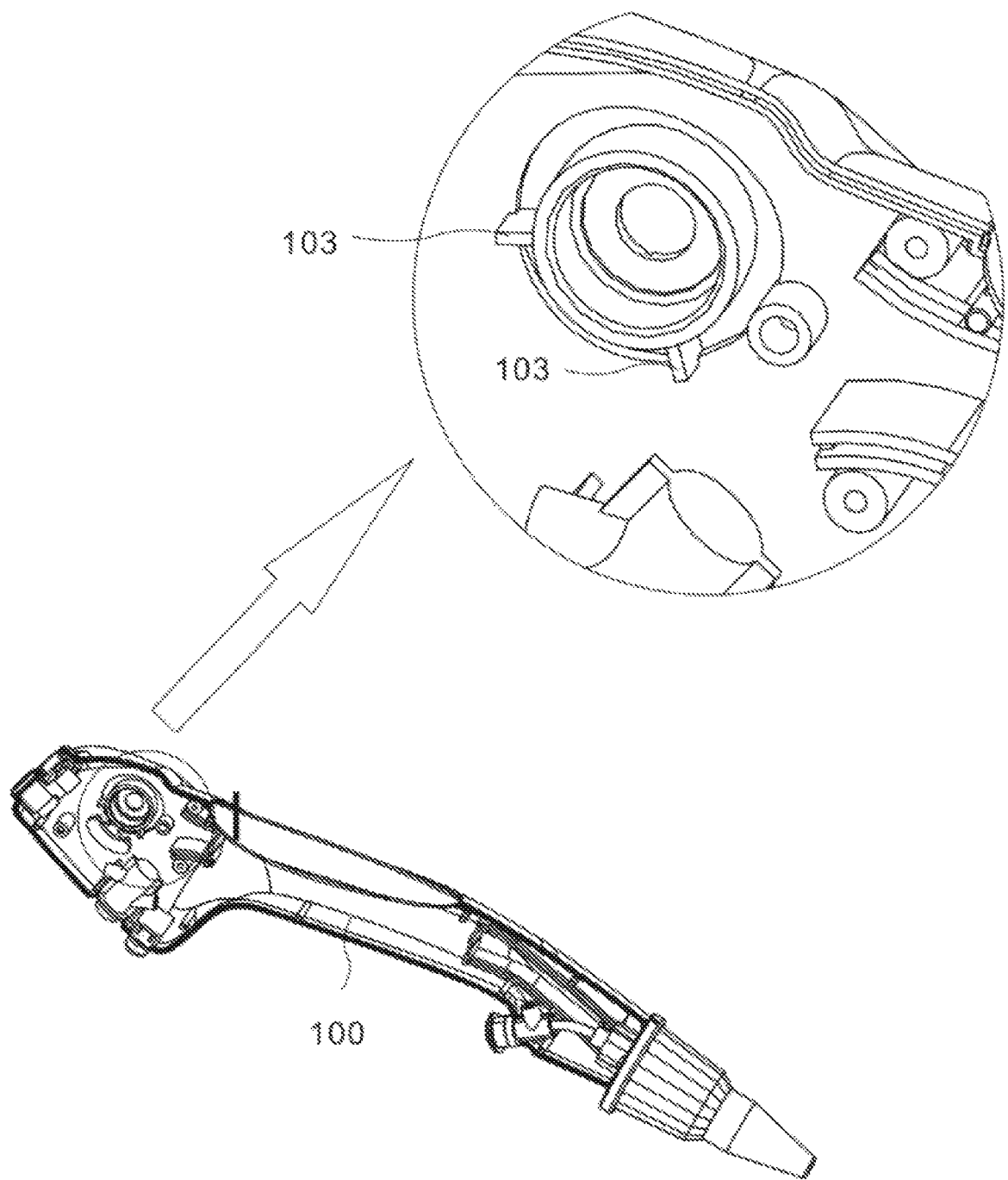
FIG. 6 is a structural view of a housing of the handheld end of an endoscope according to an embodiment of the present invention.
Figure 7:
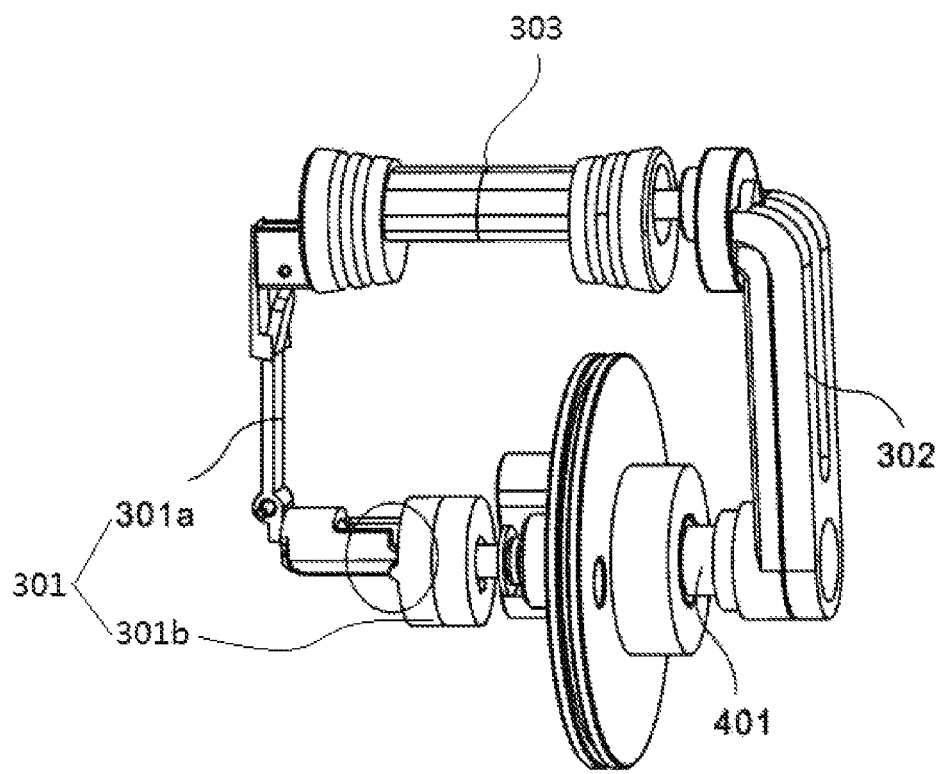
FIG. 7 is a full structural view of the self-locking assembly of the handheld end of an endoscope according to an embodiment of the present invention.
Figure 8:
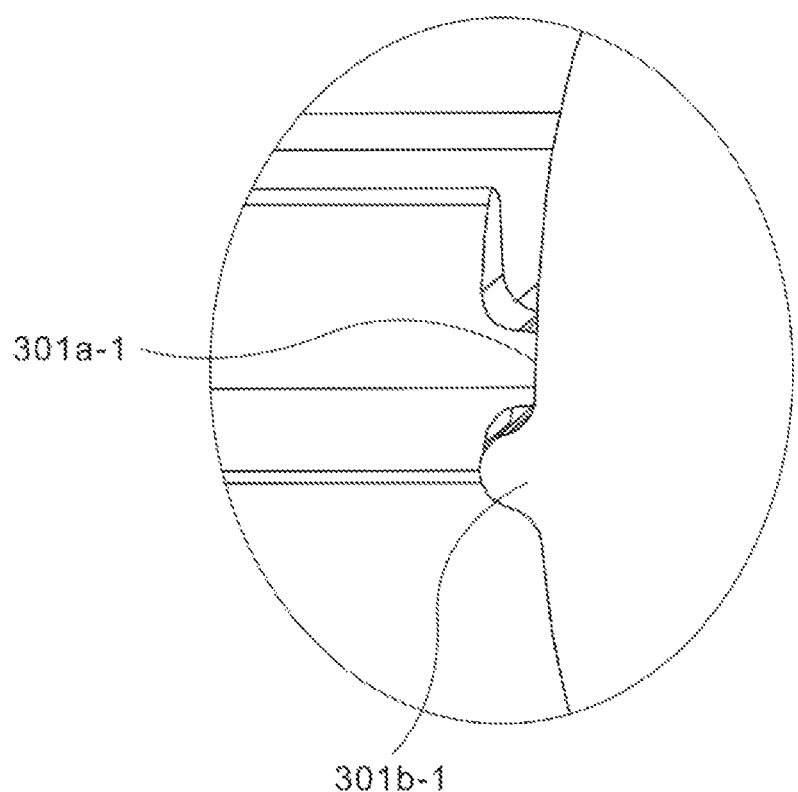
FIG. 8 is a detail of a part, shown in FIG. 7, of the handheld end of an endoscope according to an embodiment of the present invention.
Figure 9:
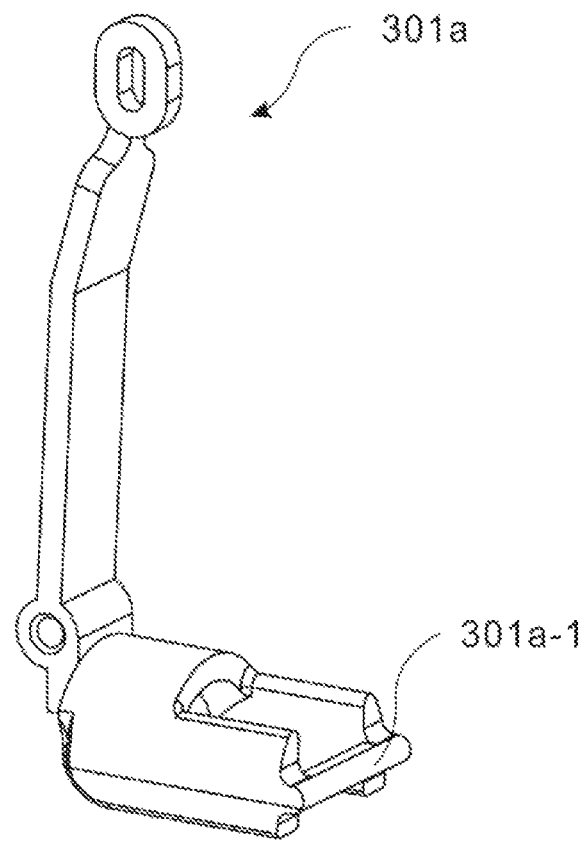
FIG. 9 is a full structural view of a toggle lever of the handheld end of an endoscope according to an embodiment of the present invention.

Referring to FIGS. 1-10, a third embodiment of the present invention provides a handheld end of an endoscope.

Different from the second embodiment, in the third embodiment, the self-locking assembly 300 includes a toggle support 301, an elastic support 302 and a toggle handle 303. The toggle handle 303 is sleeved on the toggle support 301, and is movable along a sleeving direction. A shaft of the toggle support 301 passes through the housing 100, and is connected to the elastic support 302 on the other side. An inner side of the toggle support 301 is provided with a toggle lever 301a and a friction piece 301b. One end of the toggle lever 301a is hinged to the toggle handle 303, and the other end thereof is not connected to the friction piece 301b. The toggle lever 301a has an L-shaped cross section, with a middle bend fixed to the toggle support 301. The toggle lever 301a is hinged to the toggle support 301 through a pin.

The self-locking assembly 300 includes a toggle support 301, an elastic support 302 and a toggle handle 303. The toggle handle 303 is sleeved on the toggle support 301, and is movable along a sleeving direction. A shaft of the toggle support 301 passes through the housing 100, and is connected to the elastic support 302 on the other side. That is to say, the toggle handle 303 is sleeved on the toggle support 301, and it is movable left and right along the toggle support 301.

An inner side of the toggle support 301 is provided with a toggle lever 301a and a friction piece 301b. The toggle lever 301a has an L-shaped cross section, with a middle bend fixed to the toggle support 301. The toggle lever 301a is hinged to the toggle support 301 through a pin. When the toggle lever 301a is stressed, it is rotatable around the pin, so as to push the friction piece 301b to move.

It should be noted that the toggle lever 301a and the toggle handle 303 are hinged through the pin, a connecting end of the toggle lever 301a is provided with a long oval hole, and the toggle handle 303 passes through the long oval hole to be fit with the toggle support 301. Therefore, when the toggle handle 303 moves on the toggle support 301, the toggle lever 301a provided with the long oval hole is movable up and down and left and right around the pin. The left-right direction is perpendicular to the toggle support 301.

It should be noted that, in this embodiment, there is no connection between the friction piece 301b and the toggle lever 301a.

Preferably, one end of the toggle lever 301a is provided with a fitting bump 301a-1, and one end of the friction piece 301b is provided with a fitted bump 301b-1. A plane on which the fitting bump 301a-1 is located is opposite to a plane on which the fitted bump 301b-1 is located, so that the fitting bump and the fitted bump are fit with each other.

Preferably, the fitting bump 301a-1 and the fitted bump 301b-1 each have smooth curved surfaces. For example, the fitting bump 301a-1 and the fitted bump 301b-1 each have semicircular cross sections.

Preferably, the fitting bump 301a-1 and the fitted bump 301b-1 are each the same in number.

In the present invention, a self-locking principle of the handheld end of an endoscope is as follows. In an initial state, the toggle handle 303 is placed on a left side of the toggle support 301. The toggle handle 303 is manually toggled to move from the left side of the toggle support 301 to a right side of the toggle support 301, and it stays at the right side of the toggle support 301. When the toggle handle 303 moves from the left side of the toggle support 301 to the right side of the toggle support 301, one end of the long oval hole of the toggle lever 301a moves relative to the pin, so that the toggle lever 301a rotates around the pin. As shown in the figure, in an initial position, the fitting bump 301a-1 is placed under the fitted bump 301b-1. When the toggle lever 301a rotates around the pin, the fitting bump 301a-1 is placed above the fitted bump 301b-1.

It should be noted that, one end of the friction piece 301b is fixed to the other end of the elastic support 302 through a long shaft 401. During a whole movement process, in the initial state, the elastic support 302 is in contact with the housing 100, so the resistance of pulling a tail end of a cord through the self-locking assembly 300 is very large. The tail end of the cord is self-locking without external force, and it is difficult to be pulled by the self-locking assembly 300. When the fitting bump 301a-1 moves from below the fitted bump 301b-1 to above the fitted bump 301b-1, the friction piece 301b pushes the long shaft 401 such that the elastic support 302 does not contact the housing 100. In this way, the resistance of pulling the tail end of the cord through the self-locking assembly 300 is reduced, such that the tail end of the cord can move freely through the self-locking assembly 300.

Preferably, in order to control the toggle range of the self-locking assembly 300 to avoid disconnection of the cord inside the self-locking assembly 300 due to a large toggle range, in this embodiment, the self-locking assembly 300 further includes a limiting member 304. The limiting member 304 includes a fixing disc 304a and a fitted disc 304b. The fixing disc 304a and the fitted disc 304b are fit with each other, and the fixing disc 304a is fixed to the long shaft 401. A limiting block 304b-1 is provided on the fitted disc 304b.

It should be noted that, reinforcing ribs 103 are further provided inside the housing 100. There are two reinforcing ribs 103. A movement space formed between the two reinforcing ribs 103 is fit with the limiting block 304b-1, such that the movement of the limiting block 304b-1 is limited, thereby realizing the control of the toggle range of the self-locking assembly 300.

It should be noted that the above embodiments are only intended to explain, rather than to limit the technical solutions of the present invention. Although the present invention is described in detail with reference to the preferred embodiments, those skilled in the art should understand that modifications or equivalent substitutions may be made to the technical solutions of the present invention without departing from the spirit and scope of the technical solutions of the present invention, and such modifications or equivalent substitutions should be included within the scope of the claims of the present invention.

What is claimed is:

1. A handheld end of an endoscope, comprising a housing, an insertion end positioning assembly and a self-locking assembly, wherein the self-locking assembly is hinged to the housing;

the housing comprises an insertion port, and a protective shell;

the insertion end positioning assembly comprises a positioning member, a first positioning nut, a threaded steel tube, a through hole, a fixing member and a locking member; the positioning member is inserted into the insertion port; the threaded steel tube is in threaded fit with the first positioning nut; and the first positioning nut is fixed in the positioning member;

the fixing member is fit with the through hole to abut against the threaded steel tube;

an inner bottom of the locking member is provided with a straight clamping slot, and an inner wall of the locking member is provided with an internal thread;

a tail end of the positioning member is provided with a straight fixing block; and the straight fixing block is fit with the straight clamping slot; and the protective shell is provided outside the insertion port, and the protective shell is fixedly connected to the insertion port; and the protective shell is provided with an external thread, and the external thread is fit with the internal thread.

2. The handheld end of the endoscope according to claim 1, wherein the positioning member is provided with a limiting slot;

the insertion end positioning assembly further comprises a stop piece, and the stop piece is provided in the limiting slot; and a diameter of the stop piece is greater than a diameter of the insertion port.

3. The handheld end of the endoscope according to claim 2, wherein the fixing member comprises a second nut and a fixing screw; the second nut is fixed to the through hole; and the fixing screw is in threaded fit with the second nut.

4. The handheld end of the endoscope according to claim 3, wherein the self-locking assembly comprises a toggle support, an elastic support and a toggle handle; the toggle handle is sleeved on the toggle support, and the toggle handle is movable along an outer side of the toggle support; and a shaft of the toggle support passes through the housing, and the shaft of the toggle support is connected to an first end of the elastic support on an other side;

an inner side of the toggle support is provided with a toggle lever and a friction piece, and a first end of the toggle lever is hinged to the toggle handle; and the toggle lever has an L-shaped cross section.

5. The handheld end of the endoscope according to claim 2, wherein the self-locking assembly comprises a toggle support, an elastic support and a toggle handle; the toggle handle is sleeved on the toggle support, and the toggle handle is movable along an outer side of the toggle support; and a shaft of the toggle support passes through the housing, and the shaft of the toggle support is connected to an end of the elastic support on an other side;

an inner side of the toggle support is provided with a toggle lever and a friction piece, and a first end of the toggle lever is hinged to the toggle handle; and the toggle lever has an L-shaped cross section.

6. The handheld end of the endoscope according to claim 1, wherein the self-locking assembly comprises a toggle support, an elastic support and a toggle handle; the toggle handle is sleeved on the toggle support, and the toggle handle is movable along an outer side of the toggle support; and a shaft of the toggle support passes through the housing, and the shaft of the toggle support is connected to an first end of the elastic support on an other side;

an inner side of the toggle support is provided with a toggle lever and a friction piece, and a first end of the toggle lever is hinged to the toggle handle; and the toggle lever has an L-shaped cross section.

7. The handheld end of the endoscope according to claim 6, wherein the self-locking assembly further comprises a limiting member; the limiting member comprises a fixing disc and a fitted disc; the fixing disc and the fitted disc are fit with each other; and the fixing disc is fixed to a long shaft; and a limiting block is provided on the fitted disc.

8. The handheld end of the endoscope according to claim 7, wherein two reinforcing ribs are provided inside the housing; and a movement space formed between the two reinforcing ribs is fit with the limiting block.

9. The handheld end of the endoscope according to claim 8, wherein a second end of the toggle lever is provided with a fitting bump, and a first end of the friction piece is provided with a fitted bump.

10. The handheld end of the endoscope according to claim 9, wherein the toggle lever and the toggle handle are hinged.

* * * * *